United States Patent
Mueller et al.

(10) Patent No.: US 6,871,652 B1
(45) Date of Patent: Mar. 29, 2005

(54) METHOD FOR PERMANENTLY SHAPING KERATIN FIBERS, AND AGENTS

(75) Inventors: Burkhard Mueller, Hamburg (DE); Thorsten Knappe, Hamburg (DE); Hartmut Manneck, Klein Wesenberg (DE); Dirk Bichels, Duesseldorf (DE)

(73) Assignee: Hans Schwarzkopf GmbH & Co. KG, Hamburg (DE)

( * ) Notice: Subject to any disclaimer, the term of this patent is extended or adjusted under 35 U.S.C. 154(b) by 0 days.

(21) Appl. No.: 10/030,038

(22) PCT Filed: Aug. 10, 1999

(86) PCT No.: PCT/EP99/05785

§ 371 (c)(1),
(2), (4) Date: May 20, 2002

(87) PCT Pub. No.: WO99/58099

PCT Pub. Date: Nov. 18, 1999

(30) Foreign Application Priority Data

Jul. 3, 1999 (DE) .......................... 199 30 769

(51) Int. Cl.⁷ ............................. A61K 7/08; A61K 7/09; A61K 7/11
(52) U.S. Cl. ..................... 132/202; 132/203; 132/204; 132/205; 132/209; 132/210
(58) Field of Search ................................ 132/202, 203, 132/204, 205, 209, 210; 424/70.1, 70.5, 70.31, 70.4; 536/17.9; 514/777

(56) References Cited

U.S. PATENT DOCUMENTS

| | | | | |
|---|---|---|---|---|
| 4,859,459 A | * | 8/1989 | Greiche et al. ........... | 424/70.51 |
| 5,093,113 A | | 3/1992 | Rubinstein et al. ........... | 424/72 |
| 5,681,554 A | * | 10/1997 | Cannell et al. .......... | 424/70.14 |

FOREIGN PATENT DOCUMENTS

| | | |
|---|---|---|
| CA | 2066226 | 3/1991 |
| DE | 30 09 763 | 9/1981 |
| DE | 39 29 973 | 3/1991 |
| DE | 44 36 065 | 4/1996 |
| DE | 195 34 723 | 1/1997 |
| DE | 197 10 154 | 9/1998 |
| EP | 0 363 057 | 4/1994 |
| JP | 60 81117 | 5/1985 |

OTHER PUBLICATIONS

Patent Abstracts of Japan, vol. 009, No. 218 (C–301), of JP 60 081117 (Sep. 1985).
Umbach, Kosmetik, 2$^{nd}$ Edition, pp. III–XVIII, George Thieme Verlag, Stuttgart, New York (1995).
Umbach, Kosmetik, 2$^{nd}$ Edition, pp. 259–275, George Thieme Verlag, Stuttgart, New York (1995).
K. Schrader, Grundlgen un Rezepturen der Kosmetika [Bases and Formulations in Cosmetics], 2$^{nd}$ Edition, pp. 10–23, Huethig Buch Verlag, Heidelberg, Germany (1989).
K. Schrader, Grundlgen un Rezepturen der Kosmetika [Bases and Formulations in Cosmetics], 2$^{nd}$ Edition, pp. 782–804, Huethig Buch Verlag, Heidelberg, Germany (1989).

* cited by examiner

Primary Examiner—Margaret Einsmann
Assistant Examiner—Eisa Elhilo
(74) Attorney, Agent, or Firm—Stephen D. Harper; Gregory M. Hill

(57) ABSTRACT

A process for permanently deforming keratin fibers and compositions suitable for use in this process are provided. The process includes treating keratin fibers, before and/or after mechanically deforming the keratin fibers, with an aqueous reducing composition containing a keratin reducing substance, rinsing the keratin fibers with a rinse after contact with the reducing composition, and applying to the keratin fibers an aqueous fixing composition containing an oxidizing agent, where at least one of the reducing composition, the fixing composition, or the rinse is in the form of a two-phase or multiphase system. The two phase or multiphase system contains at least one oil component and/or at least one alcohol having limited miscibility with water and is capable of being converted at least temporarily with mechanical agitation into a homogeneous system for application to hair.

6 Claims, No Drawings

METHOD FOR PERMANENTLY SHAPING KERATIN FIBERS, AND AGENTS

CROSS REFERENCE TO RELATED APPLICATIONS

This application is a national stage application under 35 U.S.C. § 371 of international application PCT/EP99/05785 filed on Aug. 10, 1999, the international application not being published in English. This application also claims priority under 35 U.S.C. §119 to DE 199 30 769.5 filed on Jul. 3, 1999.

BACKGROUND OF THE INVENTION

This invention relates to a process for the permanent deforming of keratin fibers, more especially human hair, by reductive cleavage and oxidative re-establishment of disulfide bonds of the keratin and to preparations suitable for this process.

The permanent deforming of keratin fibers is normally carried out by mechanically deforming the fibers and fixing the deformation by suitable auxiliaries. Before and/or after their deformation, the fibers are treated with an aqueous preparation of a keratin-reducing substance and, after a contact time, are rinsed with water or with an aqueous solution. In a second step, the fibers are treated with an aqueous preparation of an oxidizing agent. After a certain contact time, the oxidizing agent is also rinsed out and the mechanical deforming aids (curlers, rollers) are removed from the fibers.

The aqueous preparation of the keratin reducing agent is normally alkalized so that, on the one hand, enough of the thiol functions are deprotonated and, on the other hand, the fiber swells so that the keratin-reducing substance is able to penetrate deeply into the fiber. The keratin-reducing substance splits some of the disulfide bonds of the keratin to —SH groups, so that the peptide linkage is loosened and, through the stretching of the fibers by their mechanical deformation, the keratin structure is re-oriented. Under the influence of the oxidizing agent, disulfide bonds are re-established and, in this way, the deformation which the keratin structure has undergone is fixed. A known process of the type in question is the permanent waving of human hair. This process may be applied both to produce curls and waves in straight hair and to straighten curly hair.

Unfortunately, a negative side effect of the permanent waving of hair carried out in this way is that the hair often becomes brittle and dull. In addition, other properties, such as wet and dry combability, feel, flexibility, softness, luster and tear strength, are also adversely affected in many cases.

Accordingly, there has been no shortage of attempts in the past to remedy this situation.

A corresponding modification of the reducing solution leads to generally unsatisfactory waving performance. Although the addition of known additives, such as structurants, polymers, film formers and crosslinking resins, or the adjustment of the preparation to a neutral or mildly acidic pH can reduce the damage done to the hair, the hair remains more or less weakened in its structure. Although care of the hair by further aftertreatments can again improve the properties of the hair, it does take more time and, in general, involves the use of at least one other formulation.

Accordingly, there was still a need to find a process for permanently deforming keratin fibers in which the unwanted side effects mentioned would be further reduced or eliminated altogether.

It has now surprisingly been found that a significant improvement in the properties of deformed keratin fibers, such as improved combability and condition, can be achieved if at least one preparation used during the deforming process is formulated as a multiphase preparation and contains special compounds.

SUMMARY OF THE INVENTION

Accordingly, the present invention relates to a process for the permanent deforming of keratin fibers in which the fibers are treated before and/or after mechanical deforming with an aqueous preparation of a keratin-reducing substance, rinsed with a first rinse after a certain contact time, fixed with an aqueous preparation of an oxidizing agent and rinsed and optionally aftertreated, again after a certain contact time, characterized in that at least one of the two aqueous preparations or the first rinse is present in the form of a two-phase or multiphase system which contains at least one oil component and/or at least one alcohol having only limited miscibility with water and which, for application to the fibers, is converted by mechanical agitation into a homogeneous system.

DETAILED DESCRIPTION OF THE INVENTION

The following terms are used hereinafter:
"wave lotion" for the aqueous preparation of the keratin-reducing substance,
"intermediate rinse" for the first rinse and
"fixing agent" for the aqueous preparation of the oxidizing agent.

In the process according to the invention, the wave lotion, the intermediate rinse and/or the fixing agent is/are formulated as a two-phase or multiphase system. Two-phase and multiphase systems used in accordance with the invention are systems in which at least two separate continuous phases are present. Examples of such systems are preparations which contain the following phases:

an aqueous phase and a non-aqueous phase which are present separately from one another
an aqueous phase and two non-aqueous immiscible phases which are separately present
an oil-in-water emulsion and a separate non-aqueous phase
a water-in-oil emulsion and a separate aqueous phase.

No two-phase systems in the context of the present invention are systems in which there is only one continuous phase such as, for example, pure oil-in-water or water-in-oil emulsions.

The formulations containing two-phase or multiphase systems used in the process according to the invention only develop their full effect when they are applied to the keratin fibers in homogeneous form. To this end, the formulations are converted into homogeneous systems by mechanical action, for example by simple manual shaking of the container accommodating them. In order to ensure homogeneous application to the keratin fibers, this homogeneous state must remain intact for a sufficient time before the individual phases re-form. For the teaching according to the present invention, it has proved to be sufficient for this homogeneous state to remain stable for at least 20 seconds and, more particularly, at least 30 seconds before a boundary layer and hence the formation of the individual phases is visible to the observer.

Besides water, the two-phase and multiphase systems used in accordance with the invention contain at least one oil component and/or at least one alcohol having only limited miscibility with water as a compulsory component(s).

Oil components suitable for use in accordance with the invention are, in principle, any oils and fatty compounds and mixtures thereof with solid paraffins and waxes. Preferred oil components are those which have a solubility in water at 20° C. of less than 1% by weight and, more particularly, less than 0.1% by weight. The melting point of the individual oil or fatty components is preferably below about 40° C. Oil components which are liquid at room temperature, i.e. below 25° C., can be of particular advantage for the purposes of the invention. However, where several oil and fatty components and optionally solid paraffins and waxes are used, it is generally even sufficient if the mixture of the oil and fatty components and optionally paraffins and waxes meets these requirements.

A preferred group of oil components are vegetable oils. Examples of such oils are apricot kernel oil, avocado oil, sunflower oil, olive oil, soybean oil, rapeseed oil, almond oil, jojoba oil, orange oil, wheat germ oil, peach kernel oil and the liquid fractions of coconut oil. However, other triglycerides, such as the liquid fractions of beef tallow, and synthetic triglyceride oils are also suitable.

Another particularly preferred group of oil components suitable for use in accordance with invention are liquid paraffin oils and synthetic hydrocarbons and also di-n-alkyl ethers containing a total of 12 to 36 carbon atoms and, more particularly, 12 to 24 carbon atoms such as, for example, di-n-octyl ether, di-n-decyl ether, di-n-nonyl ether, di-n-undecyl ether, di-n-dodecyl ether, n-hexyl-n-octyl ether, n-octyl-n-decyl ether, n-decyl-n-undecyl ether, n-undecyl-n-dodecyl ether and n-hexyl-n-undecyl ether and di-tert.butyl ether, diisopentyl ether, di-3-ethyldecyl ether, tert.butyl-n-octyl ether, isopentyl-n-octyl ether and 2-methylpentyl-n-octyl ether. The compounds obtainable as commercial products, 1,3-di-(2-ethylhexyl)-cyclohexane (Cetiol® S) and di-n-octyl ether (Cetiol® OE), can be preferred.

Other oil components suitable for use in accordance with the invention are fatty acid and fatty alcohol esters. The monoesters of fatty acids with alcohols containing 3 to 24 carbon atoms are preferred. This group of compounds are products of the esterification of fatty acids containing 8 to 24 carbon atoms such as, for example, caproic acid, caprylic acid, 2-ethyl hexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of natural fats and oils, in the reduction of aldehydes from Roelen's oxosynthesis or in the dimerization of unsaturated fatty acids, with alcohols such as, for example, isopropyl alcohol, glycerol, caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and the technical mixtures thereof obtained, for example, in the high-pressure hydrogenation of technical methyl esters based on fats and oils or aldehydes from Roelen's oxosynthesis and as monomer fraction in the dimerization of unsaturated fatty alcohols. According to the invention, isopropyl myristate, isononanoic acid-$C_{16-18}$-alkyl ester (Cetiol® SN), stearic acid-2-ethylhexyl ester (Cetiol® 868), cetyl oleate, glycerol tricaprylate, cocofatty alcohol caprate/caprylate and n-butyl stearate are particularly preferred.

Other oil components suitable for use in accordance with the invention are dicarboxylic acid esters, such as di-n-butyl adipate, di-(2-ethylhexyl)-adipate, di-(2-ethylhexyl)-succinate and diisotridecyl azelate, and diol esters, such as ethylene glycol dioleate, ethylene glycol diisotri-decanoate, propylene glycol di-(2-ethylhexanoate), propylene glycol diisostearate, propylene glycol dipelargonate, butane diol diisostearate and neopentyl glycol dicaprylate, and complex esters such as, for example, diacetyl glycerol monostearate.

Finally, other oil components preferably used for the purposes of the invention are silicone oils, more particularly dialkyl and alkylaryl siloxanes such as, for example, dimethyl polysiloxane and methylphenyl polysiloxane and alkoxylated and quaternized analogs thereof. Examples of such silicone oils are the products marketed by Dow Corning under the names of DC 190, DC 200 and DC 1401 and the commercial products DC 344 and DC 345 of Dow Corning, Q2-7224 (manufacturer: Dow Corning; a stabilized trimethyl silyl amodimethicone), Dow Corning® 929 emulsion (containing a hydroxyl amino-modified silicone which is also known as Amodimethicone), SN-2059 (manufacturer: General Electric), SLM-55067 (manufacturer: Wacker) and Abil® Quat 3270 and 3272 (manufacturer: Th. Goldschmidt; diquaternary polydimethyl siloxanes, Quaternium-80).

Finally, other oil components suitable for use in accordance with the invention are the dialkyl carbonates described in detail in DE-OS 197 101 54 to which reference is expressly made. Dioctyl carbonates, more especially di-2-ethylhexyl carbonate, are preferred oil components for the purposes of the present invention.

According to the invention, alcohols having only limited miscibility with water may be used as an alternative to or in addition to the oil components mentioned.

"Alcohols having only limited miscibility with water" are understood to be alcohols of which no more than 10% by weight dissolves in water at 20° C. (based on the weight of the water).

In many cases, triols and, in particular, diols have proved to be particularly suitable for the purposes of the invention. Alcohols containing 4 to 20 and more particularly 4 to 10 carbon atoms may be used in accordance with the invention. The alcohols used in accordance with the invention may be saturated or unsaturated and linear, branched or cyclic. Examples of alcohols suitable for use in accordance with the invention are 1-butanol, cyclohexanol, 1-pentanol, decanol, octanol, octenol, dodecenol, decenol, octadienol, dodecadienol, decadienol, oleyl alcohol, erucyl alcohol, ricinolyl alcohol, stearyl alcohol, isostearyl alcohol, cetyl alcohol, lauryl alcohol, myristyl alcohol, arachidyl alcohol, capryl alcohol, capric alcohol, linoleyl alcohol, linolenyl alcohol and behenyl alcohol and Guerbet alcohols thereof (this list is purely exemplary and is not intended to limit the invention in any way). However, the fatty alcohols emanate from preferably natural fatty acids, normally being obtained from the esters of the fatty acids by reduction. According to the invention, it is also possible to use the fatty alcohol cuts which are produced by reduction of naturally occurring triglycerides, such as beef tallow, palm oil, peanut oil, rapeseed oil, cottonseed oil, soybean oil, sunflower oil and linseed oil, or fatty acid esters formed from the transesterification products thereof with corresponding alcohols and which therefore represent a mixture of different fatty alcohols.

According to the invention, preferred alcohols are 2-ethylhexane-1,3-diol, 1-butanol, cyclohexanol, 1-pentanol and butane-1,2-diol. 2-Ethylhexane-1,3-diol, 1-butanol and cyclohexanol are particularly preferred.

The aqueous and non-aqueous phases are present in the formulations used in the process according to the invention in ratios by weight of 1:200 to 1:1, preferably 1:40 to 1:5 and more preferably 1:20 to 1:10. In cases where several non-aqueous phases are present, these figures apply to the non-aqueous phases as a whole.

The teaching according to the invention also encompasses those embodiments of the process according to the invention in which the multiphase preparation is made up just before use from two or more separately produced starting preparations. This embodiment can be preferred in the case of highly incompatible components.

The present invention also relates to the preparations used to carry out the process according to the invention.

In a process for permanently deforming keratin fibers, these preparations are used either to carry out the reducing step, to carry out the oxidizing step or for rinsing after the reducing step and, in principle, may contain any of the ingredients typical of such preparations providing the requirements according to the invention (presence of the two-phase or multiphase system and rapid miscibility) are satisfied.

The process according to the invention is preferably used for permanently waving or straightening human hair.

In one preferred embodiment of the process according to the invention, the wave lotion is formulated in the form of the two-phase or multiphase system mentioned above. It has surprisingly been found that wave lotions formulated in this way have a much stronger wave effect for the same amount of the particular keratin-reducing components. Similarly, the waving performance achieved with a wave lotion which has not been formulated in accordance with the invention can be achieved with one which has despite a distinct reduction in the amount of keratin-reducing substance, which is beneficial both to the hair and to the scalp.

In addition, it has been found that, by formulating the wave lotion as a two-phase or multiphase system, the difficulties involved in perfuming can be distinctly reduced. However, perfuming is virtually indispensable because the perfume note of the compulsory ingredients of the wave lotion (keratin-reducing thio compounds, optionally alkalis, such as ammonia or alkanolamines) is not acceptable to most users. The problem is that most of the perfume components in these wave lotions are not stable in storage. Accordingly, the choice of perfume notes for such lotions is seriously restricted. It has now surprisingly been found that, where the two-phase or multiphase systems according to the invention are used, a number of other perfume components can be stably incorporated in the wave lotion. Additional perfume components have also been found to lend themselves to stable incorporation in fixing solutions made up in accordance with the invention. In the case of intermediate rinses containing the two-phase and multiphase systems according to the invention, it has been found that there is often no need to use emulsifiers or solubilizers for incorporating the perfume components.

Accordingly, in a second embodiment, the present invention relates to a preparation for carrying out the reducing step of a process for permanently deforming keratin fibers containing a keratin-reducing substance and typical ingredients, characterized in that it is present in the form of a two-phase or multiphase system which contains at least one oil component and/or at least one alcohol having only limited miscibility with water and which can be converted by mechanical action into a homogeneous system.

The wave lotions according to the invention contain mercaptans known as keratin-reducing substances as a compulsory component. Examples of such compounds are thioglycolic acid, thiolactic acid, thiomalic acid, mercaptoethane sulfonic acid and salts and esters thereof, cysteamine, cysteine, Bunte salts and salts of sulfurous acid. The alkali metal or ammonium salts of thioglycolic acid and/or thiolactic acid and free acids are particularly suitable. They are used in the wave lotions in concentrations of preferably 0.5 to 1.0 mol/kg at a pH value of 5 to 12 and, more particularly, 7 to 9.5. In order to adjust this pH value, the wave lotions according to the invention normally containing alkalizing agents, such as ammonia, alkali metal and ammonium carbonates and hydrogen carbonates, or organic amines, such as monoethanolamine.

In addition, the wave lotions according to the invention may contain components which boost their waving power such as, for example, heterocyclic compounds, such as imidazole, pyrrolidine, piperidine, dioxolane, dioxane, morpholine and piperazine, and derivatives of these compounds such as, for example, $C_{1-4}$ alkyl derivatives, $C_{1-4}$ hydroxyalkyl derivatives and $C_{1-4}$ aminoalkyl derivatives. Preferred substituents which may be positioned both at carbon atoms and at nitrogen atoms of the heterocyclic ring systems are methyl, ethyl, β-hydroxyethyl and β-aminoethyl groups. According to the invention, preferred derivatives of heterocyclic compounds are, for example, 1-methyl imidazole, 2-methyl imidazole, 4(5)-methyl imidazole, 1,2-dimethyl imidazole, 2-ethyl imidazole, 2-isopropyl imidazole, N-methyl pyrrolidine, 1-methyl piperidine, 4-methyl piperidine, 2-ethyl piperidine, 4-methyl morpholine, 4-(2-hydroxyethyl)-morpholine, 1-ethyl piperazine, 1-(2-hydroxyethyl)-piperazine, 1-(2-aminoethyl)-piperazine. According to the invention, other preferred imidazole derivatives are biotin, hydantoin and benzimidazole. Imidazole is most particularly preferred.

Amino acids such as, in particular, arginine, citrulline, histidine, ornithine and lysine. The amino acids may be used both as free amino acid and as salts, for example as hydrochlorides. Oligopeptides of on average 2 to 3 amino acids, which have a high percentage content (>50%, more particularly >70%) of the amino acids mentioned, have also proved to be suitable for use in accordance with the invention. According to the invention, arginine and arginine salts and arginine-rich oligopeptides are particularly preferred.

Diols such as, for example, 2-ethylhexane-1,3-diol, butane-1,3-diol, butane-1,4-diol, propane-1,2-diol, propane-1,3-diol, neopentyl glycol and ethylene glycol. 1,3-Diols, more especially 2-ethylhexane-1,3-diol and butane-1,3-diol, have proved to be particularly suitable.

Further information on these components which boost waving power can be found in DE-OS 44 36 065 and EP-B1 36057, to which reference is hereby expressly made.

The compounds which boost waving power may be present in the wave lotions according to the invention in quantities of 0.5 to 5% by weight, based on the wave lotion as a whole. Quantities of 1 to 4% by weight and, in the case of the diols, 0.5 to 3% by weight have proved to be sufficient so that these quantities are particularly preferred.

In a third embodiment, the present invention relates to a preparation for carrying out the oxidizing step of a process for permanently deforming keratin fibers containing an oxidizing agent and typical ingredients, characterized in that it is present in the form of a two-phase or multiphase system which contains at least one oil component and/or at least one alcohol having only limited miscibility with water and which can be converted by mechanical action into a homogeneous system.

A compulsory ingredient of the fixing preparation according to the invention are oxidizing agents, for example sodium bromate, potassium bromate, hydrogen peroxide, and the stabilizers normally used to stabilize aqueous hydrogen peroxide preparations. The pH value of such aqueous hydrogen peroxide preparations, which normally contain about 0.5 to 15% by weight and, in ready-to-use form, generally about 0.5 to 3% by weight of $H_2O_2$, is preferably in the range from 2 to 6 and more preferably in the range from 2 to 4. It is adjusted by inorganic acids, preferably phosphoric acid. Bromate-based fixing preparations contain the bromates in concentrations of normally 1 to 10% by weight, the pH value of the solutions being adjusted to pH 4–7. Enzyme-based (for example peroxide-based) fixing preparations containing only small quantities, if any, of oxidizing agents, more especially $H_2O_2$, are also suitable.

In a fourth embodiment, the present invention relates to a preparation for rinsing after the reducing step of a process for permanently deforming keratin fibers containing typical ingredients, characterized in that it is present in the form of a two-phase or multiphase system which contains at least one oil component and/or at least one alcohol having only limited miscibility with water and which can be converted by mechanical action into a homogeneous system.

It has also been found to be of advantage for the preparations according to the invention to contain a hair-care ingredient selected from protein hydrolyzates and derivatives thereof.

Suitable protein hydrolyzates are, in particular, elastin, collagen, keratin, milk protein, silk protein, soya protein, almond protein, pea protein, potato protein, oat protein, corn protein and wheat protein hydrolyzates. According to the invention, products on a vegetable basis can be preferred.

Suitable derivatives of the protein hydrolyzates are, in particular, condensation products thereof with fatty acids and fatty acid mixtures, such as oleic acid, myristic acid, undecylenic acid, cocofatty acid and abietic acid. The condensation products may also be present in the form of salts, more especially sodium, potassium and triethanolamine salts.

Other suitable derivatives are quaternized protein hydrolyzates. Examples of this class of compounds are the products commercially available under the names of Lamequat®L (CTFA name: Lauryldimonium Hydroxypropylamino Hydrolyzed Animal Protein; Grünau), Croquat®WKP and Gluadin®WQ. The last of these products, which is vegetable-based, can be preferred. The protein derivatives are present in the preparations according to the invention in quantities of preferably 0.1 to 10% by weight and more preferably 0.1 to 5% by weight, based on the preparation as a whole.

In addition, the preparations according to the invention contain at least one conditioning agent.

Preferred conditioning agents are cationic polymers which are generally polymers that contain a quaternary nitrogen atom, for example in the form of an ammonium group. Preferred cationic polymers are, for example, the quaternized cellulose derivatives commercially available under the names of Celquat® and Polymer JR®. The compounds Celquat® H 100, Celquat® L 200 and Polymer JR® 400 are preferred quaternized cellulose derivatives;

polysiloxanes containing quaternary groups;

polymeric dimethyl diallyl ammonium salts and copolymers thereof with esters and amides of acrylic acid and methacrylic acid. The products commercially available under the names of Merquat® 100 (poly(dimethyl diallylammonium chloride)) and Merquat® 550 (dimethyl diallylammonium chloride/acrylamide copolymer) are examples of such cationic polymers;

copolymers of vinyl pyrrolidone with quaternized derivatives of dialkylaminoacrylate and methacrylate such as, for example, vinyl pyrrolidone/dimethylaminomethyl methacrylate copolymers quaternized with diethyl sulfate. Such compounds are commercially available under the name of Gafquat® 734 and Gafquat® 755.

The vinyl pyrrolidones/vinyl imidazolinium methochloride copolymers commercially available under the name of Luviquat®;

quaternized polyvinyl alcohol;

and the polymers containing quaternary nitrogen atoms in the main polymer chain known under the names of Polyquaternium 2, Polyquaternium 17, Polyquaternium 18 and Polyquaternium 27.

Other suitable conditioning agents are so-called amphopolymers. Amphopolymers are amphoteric polymers, i.e. polymers which contain both free amino groups and free —COOH or —$SO_3H$ groups in the molecule and which are capable of forming inner salts, zwitterionic polymers which contain quaternary ammonium groups and —COOH⁻ or —$SO_3^-$ groups in the molecule and polymers which contain —COOH or $SO_3H$ groups and quaternary ammonium groups. One example of an amphopolymer suitable for use in accordance with the invention is the acrylate resin commercially available as Amphomer® which is a copolymer of tert.butylaminoethyl methacrylate, N-(1,1,3,3-tetramethylbutyl)-acrylamide and two or more monomers from the group consisting of acrylic acid, methacrylic acid and simple esters thereof. Other preferred amphopolymers consist of unsaturated carboxylic acids (for example acrylic and methacrylic acid), cationically derivatized unsaturated carboxylic acids (for example acrylamidopropyl trimethyl ammonium chloride) and optionally other ionic or nonionic monomers of the type disclosed, for example, in DE-OS 39 29 973 and the prior art literature cited therein. According to the invention, terpolymers of acrylic acid, methyl acrylate and methacrylamidopropyl trimonium chloride, which are commercially available under the name of Merquat® 2001 N, and the commercial product Merquat® 280 are particularly preferred amphopolymers.

The cationic or amphoteric polymers are present in the preparations according to the invention in quantities of preferably 0.1 to 5% by weight, based on the preparation as a whole.

Silicone oils and silicone gums suitable as conditioning agents are, in particular, dialkyl and alkylaryl siloxanes, such as for example dimethyl polysiloxane and methylphenyl polysiloxane, and alkoxylated and quaternized analogs thereof. Examples of such silicones are the products marketed by Dow Corning under the names of DC 190, DC 200 and DC 1401 and the commercial product Fancorsil® LIM-1.

According to the invention, other suitable conditioning agents are cationic silicone oils such as, for example, the commercially available products Q2-7224 (manufacturer: Dow Corning; a stabilized trimethyl silyl amodimethicone), Dow Corning®) 929 emulsion (containing a hydroxyl amino-modified silicone which is also known as Amodimethicone), SN-2059 (manufacturer: General Electric), SLM-55067 (manufacturer: Wacker) and Abil® Quat 3270 and 3272 (manufacturer: Th. Goldschmidt;

diquaternary polydimethyl siloxanes, Quaternium-80). A suitable anionic silicone oil is the product Dow Corning® 1784.

Examples of the cationic surfactants suitable for use as conditioning agents in the preparations according to the invention are, in particular, quaternary ammonium compounds. Preferred cationic surfactants are ammonium halides, more especially chlorides and bromides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. In addition, the readily biodegradable quaternary ester compounds, so-called "esterquats", for example the methyl hydroxyalkyl dialkoyloxyalkyl ammonium methosulfates marketed under the registered names of Dehyquart® and Stepantex®, may also be used.

Alkylamidoamines, more particularly fatty acid amidoamines, such as the stearylamidopropyl dimethyl amine commercially available under the name of Tego Amid® S 18, are distinguished not only by their favorable conditioning effect, but also and in particular by their ready biodegradability.

In addition, it can be of advantage to color the individual phases with dyes in order to provide the preparation with a particularly favorable appearance. These dyes are preferably soluble only in the aqueous phase or only in at least one non-aqueous phase in a quantity which makes the corresponding coloration visible to the observer. It is also possible to color both the non-aqueous phase and the aqueous phase with different dyes, preferably in different colors. However, it is preferred only to color a non-aqueous phase.

Other typical ingredients of the preparations according to the invention are:

anionic surfactants such as, for example, soaps, alkyl sulfates and alkyl polyglycol ether sulfates, salts of ether carboxylic acids corresponding to the formula R—O—(CH$_2$CH$_2$O)$_x$—CH$_2$—COOH, in which R is a linear alkyl group containing 10 to 22 carbon atoms and x=0 or 1 to 16, acyl sarcosides, acyl taurides, acyl isethionates, sulfosuccinic acid mono- and dialkyl esters, linear alkane sulfonates, linear alpha-olefin sulfonates, alpha-sulfofatty acid methyl esters and esters of tartaric acid and citric acid, alkyl glycosides or alcohols which are products of the addition of about 2 to 15 molecules of ethylene oxide and/or propylene oxide onto fatty alcohols containing 8 to 22 carbon atoms.

zwitterionic surfactants such as, for example, betaines and 2-alkyl-3-carboxymethyl-3-hydroxyethyl imidazolines.

ampholytic surfactants such as, for example, N-alkyl glycines, N-alkyl propionic acids, N-alkyl aminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids.

nonionic surfactants such as, for example, products of the addition of 2 to 30 mol of ethylene oxide and/or 0 to 5 mol of propylene oxide onto linear fatty alcohols containing 8 to 22 carbon atoms, onto fatty acids containing 12 to 22 carbon atoms and onto alkylphenols containing 8 to 15 carbon atoms in the alkyl group, C$_{12-22}$ fatty acid monoesters and diesters of addition products of 1 to 30 mol of ethylene oxide with glycerol, C$_{8-22}$ alkyl monoglycosides and oligoglycosides and ethoxylated analogs thereof and addition products of 5 to 60 mol of ethylene oxide with castor oil and hydrogenated castor oil.

nonionic polymers such as, for example, vinyl pyrrolidone/vinyl acrylate copolymers, polyvinyl pyrrolidone and vinyl pyrrolidone/vinyl acetate copolymers, anionic polymers such as, for example, polyacrylic and polymethacrylic acids, salts thereof, copolymers thereof with acrylates and methacrylates and acrylic and methacrylic acid amides and derivatives thereof obtained by crosslinking with polyfunctional agents, polyoxycarboxylic acids, such as polyketo- and polyaldehydocarboxylic acids and salts thereof, and polymers and copolymers of crotonic acid with esters and amides of acrylic and methacrylic acid, such as vinyl acetate/crotonic acid and vinyl acetate/vinyl propionate/crotonic acid copolymers, organic thickeners, such as agar agar, guar gum, alginates, cellulose ethers, such as methyl and methyl hydroxypropyl cellulose, gelatine, pectins and/or xanthan gum. Ethoxylated fatty alcohols, particularly narrow-range types, for example the product commercially available as Arlypon® (HENKEL), alkoxylated methyl glucoside esters, such as the commercial product Glucamate® DOE 120 (Amerchol), and ethoxylated propylene glycol esters, such as the commercial product Antil® 141 (Goldschmidt), can be preferred organic thickeners, structurants, such as glucose and maleic acid, hair-conditioning compounds, such as phospholipids, for example soya lecithin, egg lecithin and kephalins, perfume oils, solubilizers, such as ethanol, isopropanol, ethylene glycol, propylene glycol, glycerol, diethylene glycol and ethoxylated triglycerides and also fatty alcohol ethoxylates and derivatives thereof, antidandruff agents, such as Climbazol, Piroctone Olamine and Zinc Omadine, active substances, such as bisabolol, allantoin, panthenol, niacinmid, tocopherol and plant extracts, UV filters, consistency factors, such as sugar esters, polyol esters or polyol alkyl ethers, fats and waxes, such as spermaceti, beeswax, montan wax, paraffins, esters, glycerides and fatty alcohols, fatty acid alkanolamides, complexing agents, such as EDTA, NTA, β-alanine diacetic acid and phosphonic acids, swelling and penetration agents, such as PCA, glycerol, propylene glycol monoethyl ether, carbonates, hydrogen carbonates, guanidines, ureas and primary, secondary and tertiary phosphates, opacifiers, such as latex or styrene/acrylamide copolymers, pearlescers, such as ethylene glycol mono- and distearate or PEG-3 distearate, substantive dyes and propellents, such as propane/butane mixtures, N$_2$O, dimethyl ether, CO$_2$ and air.

Information on the other ingredients of the preparations according to the invention and the quantities in which they are normally used can be found in known monographs, for example Umbach, Kosmetik, 2nd Edition, Georg Thieme Verlag, Stuttgart/New York, 1995 and Kh. Schrader, Grundlagen und Rezepturen der Kosmetika, 2nd Edition, Hüthig Buch Verlag, Heidelberg, 1989.

The following Examples are intended to illustrate the invention.

EXAMPLES

All quantities are in parts by weight unless otherwise indicated.

1. Mildly Alkaline Wave Lotion (Two Phases)

|  | Invention | Comparison |
|---|---|---|
| Ammonium thioglycolate (71% in water) | 16.0 | 16.0 |
| Ammonium hydrogen carbonate | 6.0 | 6.0 |
| Lamepon ® S[1] | 0.8 | 0.8 |
| Nutrilan ® KW[2] | 0.5 | 0.5 |
| Natrosol ® 250 HR[3] | 0.15 | 0.15 |
| Soybean oil | 3.0 | — |
| Paraffin oil 35 cP | 10.0 | — |
| Apricot kernel oil | 2.0 | — |
| Perfume oil | 0.2 | 0.2 |
| Ammonia (25% in water) | to pH8.2 | to pH8.2 |
| Water | to 100 | to 100 |

[1]Collagen hydrolyzate/cocofatty acid condensate, sodium salt (ca. 32% active substance in water; INCI name: Potassium Cocoyl Hydrolyzed Collagen) (HENKEL)
[2]Keratin hydrolyzate (20% active substance in water; INCI name: Hydrolyzed Keratin) (HENKEL)
[3]Hydroxyethyl cellulose (INCI name: Hydroxyethylcellulose) (HERCULES)

The wave lotion according to the invention had two phases (oil phase, water phase). The wave lotion according to the invention produced a distinctly better waving result than the one-phase wave lotion of the Comparison Example. In addition, the hair had a particularly "cared-for" appearance. It was smoother and had a particularly good feel.

2. Neutral Wave Lotion (Two Phases)

|  | Invention | Comparison |
|---|---|---|
| Ammonium thioglycolate (71% in water) | 18.0 | 18.0 |
| Thiolactic acid | 5.0 | 5.0 |
| Imidazole | 5.0 | 5.0 |
| Eumulgin ® L[4] | 0.8 | 0.8 |
| Propylene glycol | 0.7 | 0.7 |
| Kollaplex ® 1.0-S[5] | 0.3 | 0.3 |
| Soybean oil | 8.5 | — |
| Avocado oil | 1.5 | — |
| Perfume oil | 0.4 | 0.4 |
| Ammonia (235% in water) | to pH7.5 | to pH75 |
| Water | to 100 | to 100 |

[4]2-Hydroxyfatty alcohol ethoxylate (INCI name: PPG-1-PEG-9-Lauryl Glycol Ether) (HENKEL)
[5]Collagen fixed to polysaccharides (INCI name; Soluble Collagen) (GfN)

The wave lotion according to the invention had two phases (oil phase, water phase). The wave lotion according to the invention produced a distinctly better waving result than the one-phase wave lotion of the Comparison Example. In addition, the hair looked particularly cared-for.

3. Wave Lotion (Two Phases)

| | |
|---|---|
| Ammonium thioglycolate (71% in water) | 16.0 |
| Ammonium hydrogen carbonate | 5.5 |
| Lamepon ® S | 1.4 |
| Monomuls ® 90 O 18[6] | 1.4 |
| Natrosol ® 250 HR | 0.3 |
| Merquat ® 100[7] | 0.3 |
| Gluadin ® WQ[8] | 0.5 |
| Soybean oil | 5.0 |
| Perfume oil | 0.3 |
| Ammonia (25% in water) | to pH8.4 |
| Water | to 100 |

[6]Glycerol monooleate (INCI name: Glyceryl Oleate) (HENKEL)
[7]Poly(dimethyl diallyl ammonium chloride) (40% active substance; INCI name: Polyquaternium-6) (CHEMVIRON)
[8]Quaternized wheat protein hydrolyzate (ca. 33% active substance in water; INCI name: Lauryldimonium Hydroxypropyl Hydrolyzed Wheat Protein) (GRÜNAU)

4. Wave Lotion (Three Phases)

| | |
|---|---|
| Ammonium thioglycolate (71% in water) | 16.0 |
| Ammonium hydrogen carbonate | 5.5 |
| Lamepon ® S | 1.4 |
| Natrosol ® 250 HR | 0.3 |
| Merquat ® 100 | 0.3 |
| Gluadin ® WQ | 0.5 |
| Soybean oil | 5.0 |
| Dow Corning ® 344[9] | 5.0 |
| Perfume oil | 0.3 |
| Ammonia (25% in water) | to pH8.4 |
| Water | to 100 |

[9]Octamethyl cyclotetrasiloxane (INCI name: Cyclomethicone) (DOW CORNING)

5. Wave Lotion (Two Phases)

| | |
|---|---|
| Ammonium thioglycolate (71% in water) | 16.0 |
| Ammonium hydrogen carbonate | 9.0 |
| Lamepon ® S | 1.0 |
| Merquat ® 100 | 0.5 |
| Gluadin ® WQ | 0.5 |
| 2-Ethylhexane-1,3-diol | 5.0 |
| Dye | 0.0002 |
| Perfume oil | 1.0 |
| Ammonia (25% in water) | to pH8.4 |
| Water | to 100 |

The wave lotion produced intensive uniform waves with considerable bounce. The hair looked very cared-for after the treatment and was easy to comb.

6. Intermediate Rinse

| | |
|---|---|
| Dioctyl carbonate | 5.0 |
| Paraffin oil | 2.0 |
| Water | 93.0 |

By applying the intermediate rinse, the hair was easy to comb and looked very cared-for after the treatment.

7. Fixing Lotion (Three Phases)

| | |
|---|---|
| Hydrogen peroxide (50% in water) | 4.0 |
| Aromox ® MCD-W[10] | 1.0 |
| Turpinal ® SL[11] | 1.0 |
| Dioctyl carbonate | 5.0 |
| Paraffin oil | 2.0 |
| 2-Ethylhexane-1,3-diol | 5.0 |
| Water | 82.0 |

[10]N,N-dimethyl-N-cocoalkylamine-N-oxide (30% active substance in water; INCI name: Cocamine Oxide) (AKZO)
[11]1-Hydroxyethane-1,1-diphosphonic acid (ca. 60% active substance in water; INCI name: Etidronic Acid) (HENKEL)

After the fixing treatment according to the invention, the hair was very easy to comb and looked very "cared-for".

8. Wave Lotion for Porous Hair (Two Phases)

| | |
|---|---|
| Ammonium thioglycolate (71% in water) | 10.0 |
| Ammonium hydrogen carbonate | 3.0 |
| Lamepon ® S | 1.0 |
| Merquat ® 100 | 0.5 |
| Gluadin ® WQ | 0.5 |
| 2-Ethylhexane-1,3-diol | 4.0 |
| Dye | 0.0001 |
| Perfume oil | 1.0 |
| Imidazole | 5.0 |
| Water | to 100 |

The wave lotion produced intensive uniform waves with considerable bounce in porous hair. The hair looked very cared-for and was easy to comb after the treatment.

9. Multicomponent Wave Lotion (Two Phases)

| Component A (two phases) | |
|---|---|
| Ammonium bicarbonate | 6.0 |
| Ammonia | 1.0 |
| 2-Ethylhexane-1,3-diol | 10.0 |
| Perfume | 1.0 |
| Merquat ® 100 | 0.1 |
| Croquat ® WKP[12] | 0.1 |
| Water | to100.0 |

[12]Quaternized keratin hydrolyzate (ca. 32% active substance in water; INCI name: Cocodimonium Hydroxypropyl Hydrolyzed Keratin) (CRODA)

| Component B | |
|---|---|
| Ammonium thioglycolate (71% in water) | 50 |
| Ammonium thiolactate (70% in water) | 25 |
| Water | to100 |

Before use, 52 ml of component A was mixed with 23 ml of component B. The ready-to-use mixture formed was only temporarily homogeneous and visibly separated into two phases after a few minutes. The wave lotion produced intensive uniform waves with considerable bounce. The hair looked very cared-for and was easy to comb after the treatment.

10. Heat-Activated 2-Component Wave Lotion for Porous Hair (Two Phases)

| Component A (two phases) | |
|---|---|
| Ammonium thioglycolate (71% in water) | 21.7 |
| Ammonia | 2.8 |
| 2-Ethylhexane-1,3-diol | 8.0 |
| Perfume | 1.0 |
| Merquat ® 100 | 2.5 |
| Lamepon ® S | 1.0 |
| Water | to 100 |

| Component B | |
|---|---|
| hydrogen peroxide 50% | 7.2 |
| Phosphoric acid 85% | 0.15 |
| PHB methyl ester | 0.04 |
| Water | to 100 |

Before use, 60 ml of component A was mixed with 15 ml of component B. The ready-to-use mixture formed, of which the temperature was 15 to 20° C. higher than before mixing, was only temporarily homogeneous and visibly separated into two phases after a few minutes. The wave lotion produced intensive uniform waves with considerable bounce in porous hair. The hair looked very cared-for and was easy to comb after the treatment.

What is claimed is:

1. A process for permanently deforming keratin fibers comprising the steps of:
   (a) contacting keratin fibers with a reducing composition for a first contact time, wherein the reducing composition comprises at least one keratin-reducing substance and is applied before or after, or before and after mechanically deforming the keratin fibers;
   (b) rinsing the keratin fibers with a first rinse after the first contact time;
   (c) contacting the keratin fibers for a second contact time with a fixing composition comprising an oxidizing agent for fixing the keratin fibers, wherein at least one of the reducing composition, the fixing composition or the first rinse is in the form of a two-phase or multiphase system and comprises at least one alcohol having 4 to 10 carbon atoms and having only limited miscibility with water, and wherein the two phase or multiphase system is capable of being converted by mechanical agitation into a homogeneous system for application to the fibers; and
   (d) rinsing the keratin fibers with a second rinse after the second contact time.

2. The process of claim 1, wherein the two phase or multiphase system further comprises at least one oil.

3. The process of claim 2 wherein the oil is selected from one or more vegetable oils, paraffin oils or silicones, or combinations thereof.

4. The process of claim 3 wherein the alcohol having only limited miscibility with water comprises a diol or trial.

5. The process of claim 1 wherein the alcohol having only limited miscibility with water comprises a diol or triol.

6. The process of claim 1 wherein the alcohol having only limited miscibility with water is branched.

* * * * *